United States Patent [19]

Ide et al.

[11] Patent Number: 4,821,021

[45] Date of Patent: Apr. 11, 1989

[54] SELECTIVE CALLING RADIO DISPLAY PAGER HAVING A MESSAGE RECALLING ALGORITHM WHICH SIMPLIFIES OPERATIONS

[75] Inventors: Motoki Ide; Toshifumi Sato, both of Tokyo, Japan

[73] Assignee: NEC Corporation, Japan

[21] Appl. No.: 140,022

[22] Filed: Dec. 31, 1987

[30] Foreign Application Priority Data

Jan. 13, 1987 [JP]  Japan .................................. 62-4021

[51] Int. Cl.[4] ........................................... H04G 07/02
[52] U.S. Cl. ............................ 340/311.1; 340/825.44; 340/825.47; 340/825.48
[58] Field of Search ........... 340/311.1, 825.44, 825.47, 340/825.48, 792

[56] References Cited

FOREIGN PATENT DOCUMENTS

0136677  4/1985  European Pat. Off. ....... 340/825.44

Primary Examiner—Joseph A. Orsino
Assistant Examiner—Annie H. Chan
Attorney, Agent, or Firm—Laff, Whitesel, Conte & Saret

[57] ABSTRACT

Manually operated first, second and third command entry switches are provided for respectively generating first, second and third command signals. In response to the first command signal a controller successively recalls portions of received messages from a memory in a first sequence and causes the recalled portions to be successively displayed. The controller responds to the second command signal by successively recalling starting portions of the messages in a second sequence and causing the recalled starting portions to be successively displayed. To simplify back scrolling operations, the controller responds to the third command signal by successively recalling the portions of the messages in a direction opposite to the first sequence if the portion being displayed at the moment the third command signal is generated is not a starting portion or successively recalling the starting portions of the messages in a direction opposite to the second sequence if the portion being displayed at the moment the third command signal is generated is a starting portion.

6 Claims, 10 Drawing Sheets

WORDWRAP SUBROUTINE

FIG.7F

REVERSE WORDWRAP SUBROUTINE

SELECTIVE CALLING RADIO DISPLAY PAGER HAVING A MESSAGE RECALLING ALGORITHM WHICH SIMPLIFIES OPERATIONS

BACKGROUND OF THE INVENTION

The present invention relates generally to selective calling radio display pagers, and more specifically to such papers which are capable of recalling received messages in a simplified procedure.

In a known radio display pager, received messages are stored into a memory and recalled later by operating command entry switches. Since the area of display is limited, it is the usual practice to divide each message into portions, or "blocks" for successively putting them onto display in response to successive operations of the command entry switches. These switches are designated Read, Index and Reverse, respectively. The Read switch is used to recall message blocks so that the beginning of each a message appears first. When the Index switch is operated, the beginnings of the messages can be recalled in succession to permit the user to rapidly scroll through the received messages. The Reverse switch is used to scroll in the opposite direction when it is desired to review the previously displayed block while operating either the Read or Index switch. However, the prior art pager requires one step too many because of the need to operate the Read or Index switch again to effect the back scroll.

SUMMARY OF THE INVENTION

It is, therefore, an object of the present invention to provide a selective calling radio display pager which is easy to use.

According to the present invention, received messages are stored in a memory and recalled in response to command signals. Manually operated first, second and third command entry switches are provided for respectively generating first, second and third command signals. Either control means or a microprocessor is provided to successively recall portions of the messages from the memory in a first sequence in response to the first command signal and to cause the recalled portions to be successively displayed. In response to the second command signal, the microprocessor successively recalls starting portions of the messages from the memory in a second sequence and causes the recalled starting portions to be successively displayed.

In response to the third command signal, the microprocessor successively recalls portions of one of the messages from the memory, in a direction opposite to the first sequence, if the portion being displayed at the moment the third command signal is generated is not a starting portion of a message. The microprocessor either causes the recalled portions to be successively displayed or successively recalls the starting portions of the messages from the memory, in a direction opposite to the second sequence, if the portion being displayed at the moment when the third command signal is generated is a starting portion of a message and causes the recalled starting portions to be successively displayed.

If it is desired to back scroll while messages are recalled by using the first or second command entry switch, all that is required is for the user to manipulate the third command entry switch. No more is required.

In a preferred embodiment of the invention, the stored messages are scanned in the second sequence to detect a blank of first occurrence. Part of the scanned message which is located adjacent the detected blank is excluded from a portion of the message which is displayed when message portions are recalled in a direction opposite to the first sequence or when starting portions are recalled in a direction opposite to the second sequence. This provides "wordwrap" by which the last word of a displayed portion, if it is incomplete, is automatically moved to the beginning of a message portion to be subsequently displayed.

In a further preferred embodiment, the stored messages are scanned in the first sequence to detect a blank of first occurrence and part of the scanned message which is located adjacent the detected blank is excluded from a portion of the message which is displayed when message portions other than the starting portions are recalled in a direction opposite to the first sequence. This is advantageous to provide "reverse wordwrap" when a message is scrolled toward its starting portion in response to the operation of the third command entry switch.

BRIEF DESCRIPTION OF THE DRAWINGS

The present invention will be described in further detail with reference to the accompanying drawings, in which.

DETAILED DESCRIPTION

Figure 1:
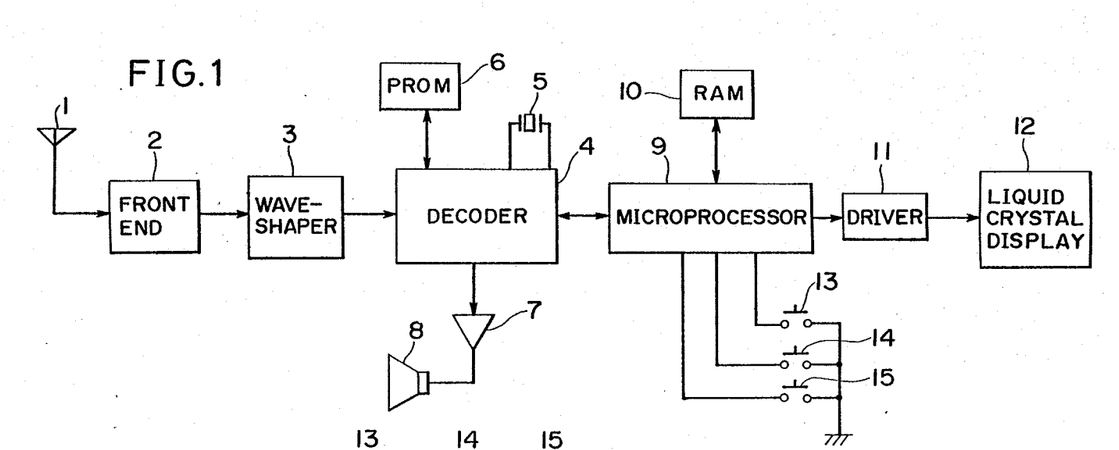
FIG. 1 is a block diagram of a selective calling radio display pager embodying the present invention.

As illustrated in FIG. 1, a selective calling radio display pager is in a standby mode ready to receive from a central transmitte, a digitally modulated radio-frequency paging signal of a known format. The signal is detected by an antennal 1, amplified and demodulated by a front end 2 and fed through a waveshaper 3 to a decoder 4. Decoder 4 is of conventional design and operates on a synchronous mode using a quartz crystal 5 to check identifiers contained in the received signal against the user's unique address permanently stored in a programmable read-only memory 6 in order to detect a match between them. When decoder 4 detects a match, it supplies a tone signal through an amplifier 7 to a loudspeaker 8 to alert the pager's owner and, at the same time, relays a message signal that accompanies the address code to a microprocessor 9.

Microprocessor 9 checks the contents of the message signal to detect the end of the message, proceeds to return an end-of-message signal to the decoder 4 and writes the message signal into a random access memory 10 along with a number indicating the sequence of arrival of the message. The smaller the sequential number, the older the message is. As will be described later, each message is thus identified by the sequential number and is divided into blocks of an appropriate length for purposes of display.

Figure 2:
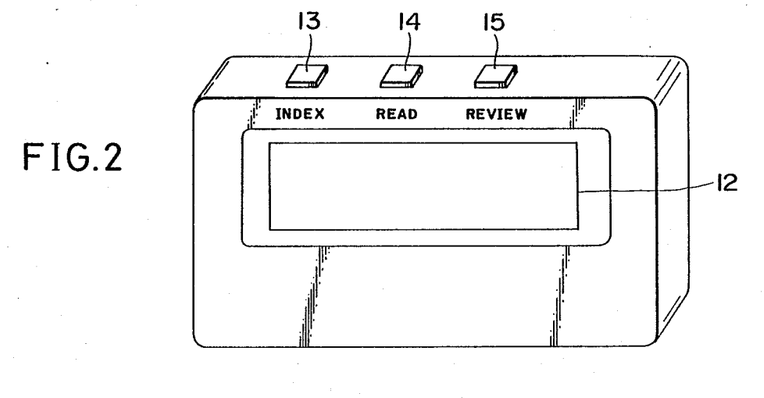
FIG. 2 is a perspective view of the radio display pager.

On one side of a pager's casing, manually operated switches 13, 14 and 15 are mounted as shown in FIG. 2. These switches, respectively labelled with legends "Index", "Read" and "Review", are connected to the microprocessor 9 for enabling an entry of command signals. The Index switch 13 is used to recall the first block of a message from the memory 10 in a backward, or "new-to-old" direction in response to each depression of switch 13. The Read switch 14 is used to recall blocks of a given message in a forward, or "old-to-new" direction in response to each depression and shift to the first block of an adjacent message in the backward direction, if switch 14 is depressed at the last block of the given message. The Review switch 15 is used to recall blocks of a given message in the "new-to-old" direction in response to each depression and shift to the first block of an adjacent message in the "old-to-new" direction when it is depressed at the firt block of the given message. Each recalled message is supplied from the microprocessor 9 to a driver 11 and displayed on a liquid crystal display 12 which is provided on one surface of the pager's casing. Liquid crystal display 12 has a rectangular display area, or "window" which displays a maximum of 16 characters.

Figure 3:
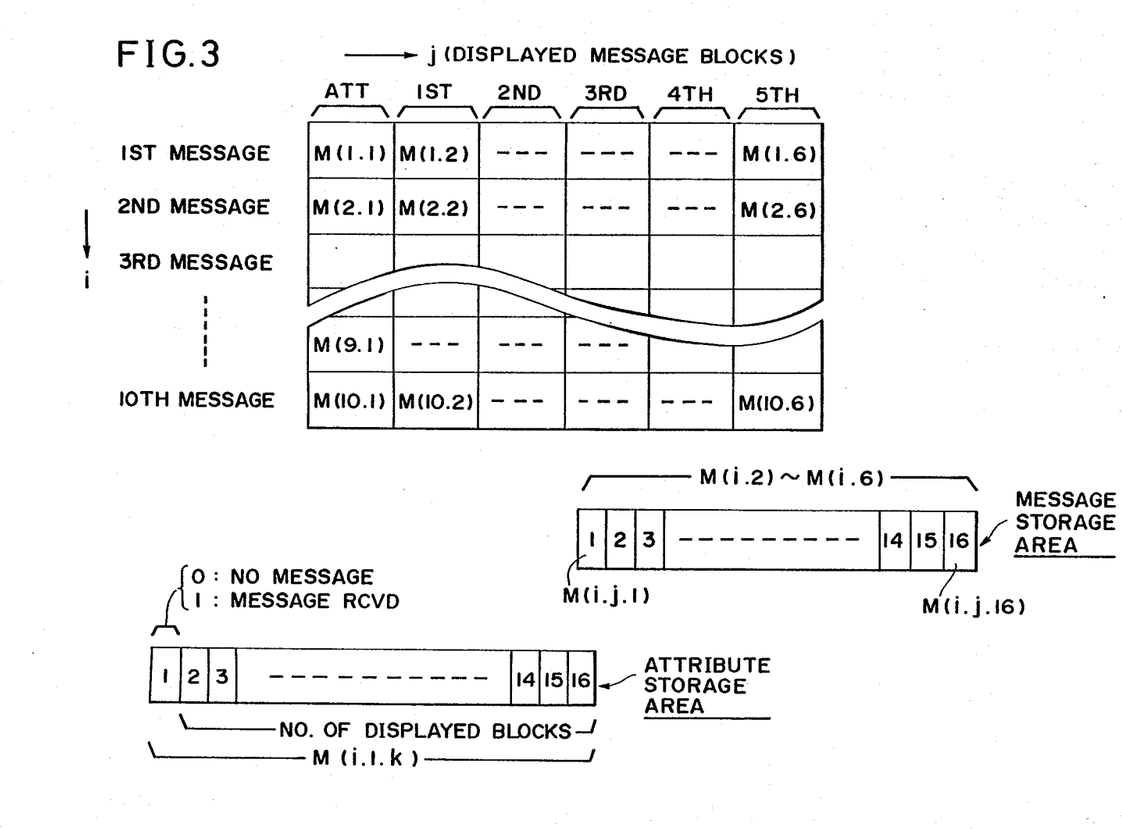
FIG. 3 is an illustration of a structure of data stored in a matrix in the random access memory of FIG. 1 according to a first embodiment of the present invention.

According to a first embodiment of the present invention, received messages are stored in the memory 10 in an array of rows and columns as shown in FIG. 3. Messages are stored into rows identified by a variable "i" indicating the sequence of arrival. Typically, ten messages are stored respectively along the first to tenth rows. Each row of the matrix is divided into six columns identified by a variable "j". The first column is identified as an attribute storage area and the second to sixth columns are identified as first through fifth message storage areas. The attribute storage area stores a message flag which is either binary 1 or binary 0 respectively indicating the presence and absence of a message in the associated first through fifth message storage areas and a message length code indicating the number of blocks of the message stored in the associated message storage areas.

Each of the storage areas stores as many as 16 characters and blanks the position of which is identified by a variable "k". It is seen that each block of a message can be identified by a notation $M(i,j)$ as a function of variables i and j and each character and blank of that message can be identified by a notation $M(i,j,k)$, where i is in the range between 1 and 10, j is in the range between 1 and 6 and k is in the range between 1 and 16.

Figure 4:
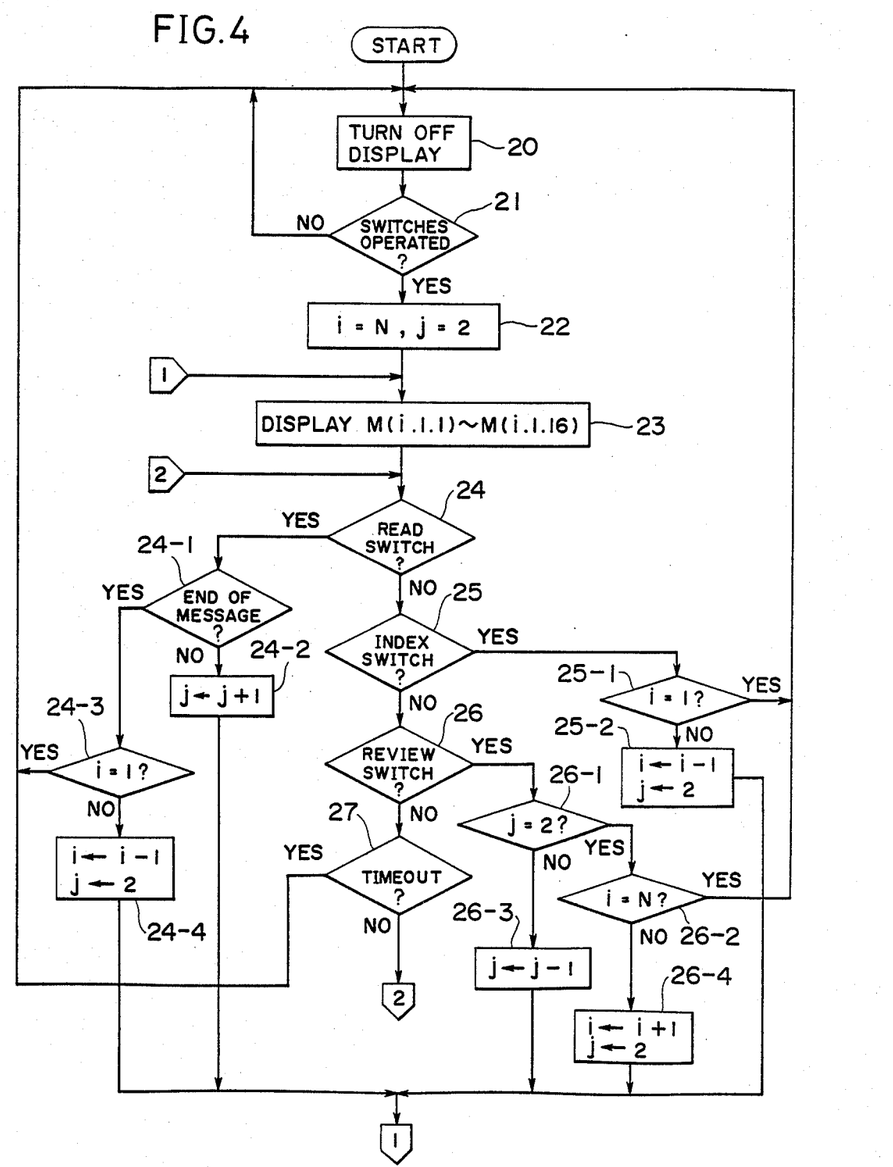
FIG. 4 is a flow diagram describing a sequence of instructions performed by the microprocessor according to the first embodiment of the invention.

FIG. 4 is a flow diagram which describes a sequence of programmed instructions to be performed by the microprocessor 9 in response to the operation of each of the command entry switches 13, 14 and 15. The program starts with operations block 20 which directs the turn-off of the liquid crystal display 12. Exit then is to decision block 21 which checks to see if any one of the command entry switches is operated or not. If there is no command entry switch being operated, control returns to operations block 20. If one of the command entry switches is operated, exit is to operations block 22 which directs the setting of the variables i and j equal to N and 2, respectively, where N is the highest of the variables i at a given instant of time and hence represents the most recent message. Exit now is to operations block 23 which directs the displaying of characters $M(i,1,1)$ through $M(i,1,16)$. Therefore, the first block of the most recent message is initially displayed on LCD 12. Exit from operations block 23 is to a sequence of decision blocks 24, 25 and 26 for checking which one of the command entry switches is operated.

If the Read switch 14 has been operated, exit from decision block 24 is to a message readout subroutine which comprises blocks 24-1 through 24-4. Block 24-1 determines if the displayed block is the end of a message. If the answer is negative, exit is to operations block 24-2 which increments the variable j by one and control returns to the message display block 23. Thus, the display "window" initially moves from on block to another along the most recent message in a forward direction in response to successive operations of the Read switch 14. If the answer is affirmative in block 24-1, control goes to decision block 24-3 to check to see if the variable j is equal to one. Thus, each operation of the Read switch 14 causes blocks 23, 24, 24-1 and 24-2 to be repeatedly executed until the last block of the most recent message comes into view, whereupon exit is to decision block 24-3 to check to see if variable i is equal to 1. If the answer is negative in block 24-3, exit is to operations block 24-4 which decrements variable i by one to scroll the display window one message in backward direction and resets variable j to 2.

Control now returns to block 23 to display the first block of a message which is one message older than the most recent one. Control proceeds through blocks 24, 24-1 and 24-2 to move the display window from one block to another of a message until the last block of the message comes into view. It is seen that as long as the Read switch 14 is repeatedly operated, messages are scrolled in a zigzag pattern until all the messages stored in the memory 10 are recalled. When this occurs, variable i becomes equal to 1 and control exits block 24-3 and returns to display turn-off block 20.

When the Index switch 13 is operated, control exits decision block 25 and enters decision block 25-1 which checks to see if variable i is equal to 1. If the answer is negative, exit is to operations block 25-2 which decrements variable i by one and resets variable j to 2 and control returns to block 23. The first block of an adjacent old message is therefore displayed. It is seen that, in response to each operation of the Index switch 13, operations block 25-2 is executed and variable i is decremented by one. The display window is scrolled in backward direction so that the first block of successively older messages comes into view in response to each operation of the Index switch 13. This permits the user to browse through the recorded messages in the new-to-old direction. This continues until the variable i becomes equal to one (block 25-1).

If the Review switch 15 is operated, control exits decision block 26 and enters decision block 26-1 which checks for the presence of variable j=2. If there is one, exit is to decision block 26-2 which tests for the presence of variable i=N. If the message currently on display is the most recent message, the answer is affirmative in block 26-2 and control returns to display turn-off block 20. On the other hand, if characters on display are not the first block of any message, the answer is negative in block 26-1 and exit is to operations block 26-3 where the variable j is decremented by one to exit to the message display block 23. As long as this condition exists, each operation of the Review switch 15 causes blocks 26-1 and 26-3 to be repeatedly executed to successively decrement the variable j until it becomes equal to 2 and control exits to decision block 26-2. Thus, the display window is moved from one block to another of a message in a backward direction in response to operation of the Review switch 15 until the first block of that message comes into view. If this message is not the most recent one, a further operation of the Review switch 15 causes control to pass through blocks 26-1 and 26-2 and enters operations block 26-4 where the variable i is incremented by one and the variable j is set equal to 2.

In like manner, if characters, which are being displayed before the Review switch is first operated, are the first block of a message other than the most recent one, control passes through blocks 26-1 and 26-2 and enters operations block 26-4. Under these conditions, the display window is scrolled in a forward direction in response to each operation of the Review switch 15 to bring the first block of successively newer messages into view. If any of the command entry switches is operated within a specified period following the display of a message block, control exits time-out block 27 of decision block 24 to repeat the scanning process. If the time-out period expires, control returns to the display turn-off block 20.

The operation of the present invention can be summarized as follows. As shown in part (a) of FIG. 5, successive operations of the Read switch 14 cause blocks of the diplay window to be moved in a forward direction and successive messages to be scrolled in a backward direction to follow a zigzag pattern as indicated by solid-line arrows. In part (b) of FIG. 5, successive operations of the Index switch 13 causes the display window to scroll in a backward direction from the first block of one message to the first block of another as indicated by the solid-line arrows. The operation of the Review switch 15 is shown in part (c) of FIG. 5 in which the display window is scrolled from one block to another of a message in a backward direction as long as the display window is located on a block other than the first block. Then it is scrolled from the first block of one message to the first block of another in a forward direction once the display window reaches the first block of the message which is initially encountered when the Review switch is operated.

Figure 5:
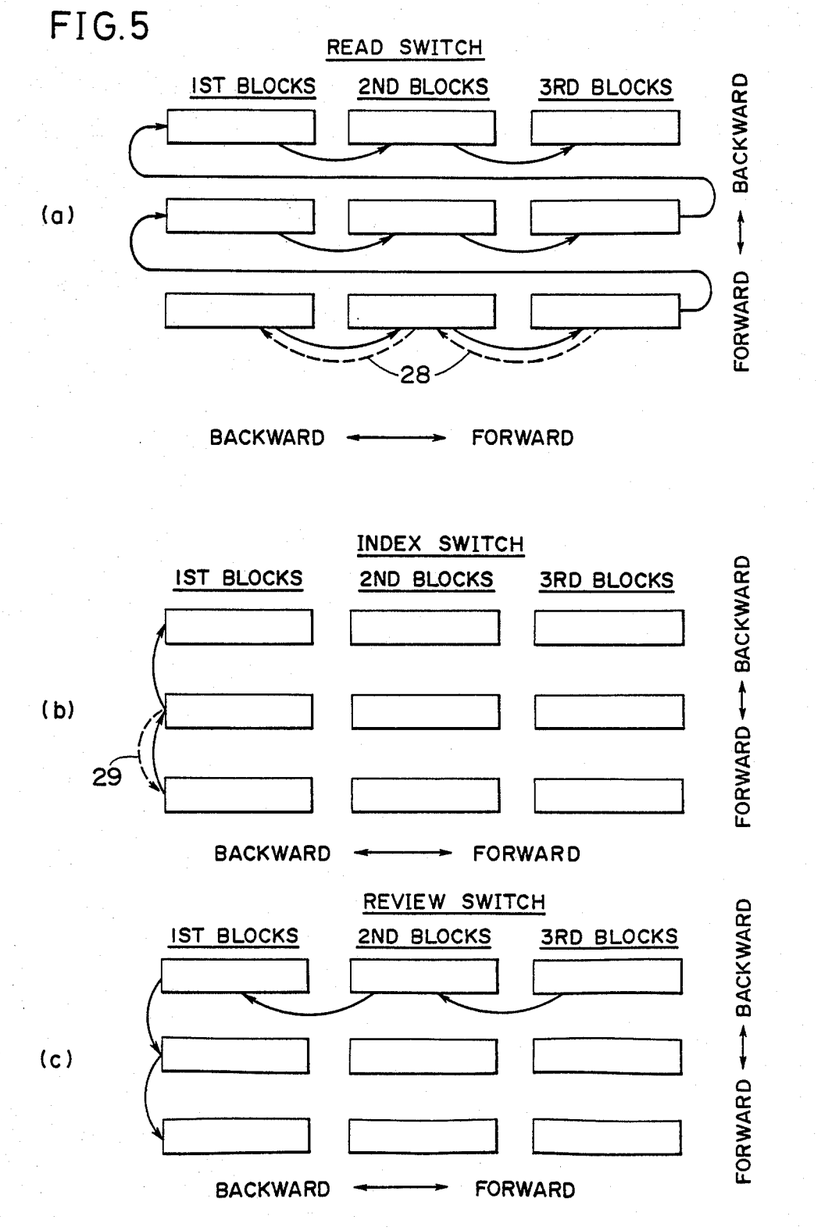
FIG. 5 is an illustration useful for understanding the advantageous effect of the invention.

If it is desired to scroll back from one message block to another as indicated by broken-line arrows 28, this can be done by simply operating the Review switch 15 in succession since it causes control to repeatedly execute operations block 26-3. On the other hand, if it is desired to scroll back from the first block of a message to the first block of another as indicated by broken-line arrows 29, this can also be done with operation of the Review switch 15 since it causes control to execute operations block 26-4. Therefore, the radio paging receiver of the invention only requires switching from one command entry switch to the Review switch if it is desired to scroll back in any direction, whereas the prior art paging receiver requires one step too many to accomplish message scroll in a reverse direction.

Figure 6:
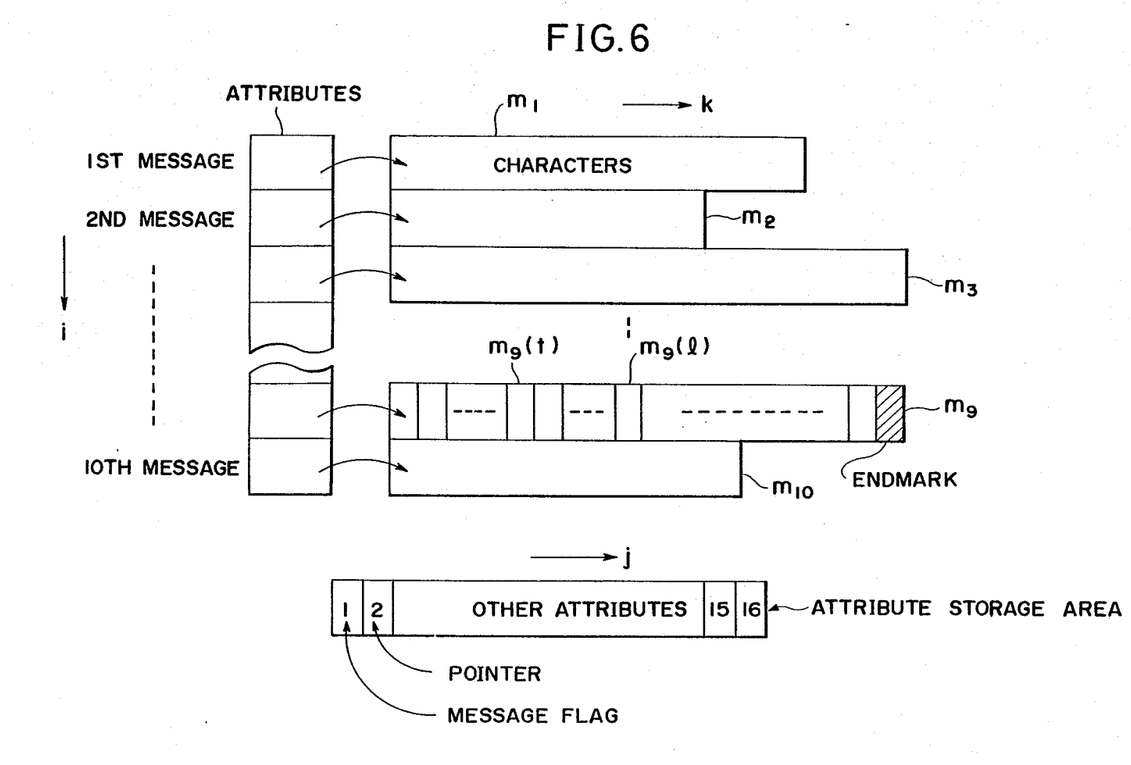
FIG. 6 is an illustration of a structure of data stored in the random access memory according to a second embodiment of the invention.

If the last word of a message block is incomplete, it is desirable to automatically move it to the next block. This is called "wordwrap". A second embodiment shown in FIG. 6 is to accomplish the wordwrap. In this embodiment, each message is stored as a continuous string of characters and blanks into the memory 10. The beginning of each message is identified by a pointer stored in an associated attribute storage area which additionally includes other attributes of the same message. Each message is terminated with an "endmark" indicating the end of message and is divided according to the length of a word or words which can be simultaneously displayed as a continuous string. The characters and blanks contained in the simultaneously displayable string are identified by $m_i(t)$ through $m_i(l)$, where t indicates the first position of the string and l indicates the last position of the string, with l being equal to $t+15$ to display a maximum of 16 characters and blanks simultaneously.

Figure 7A:
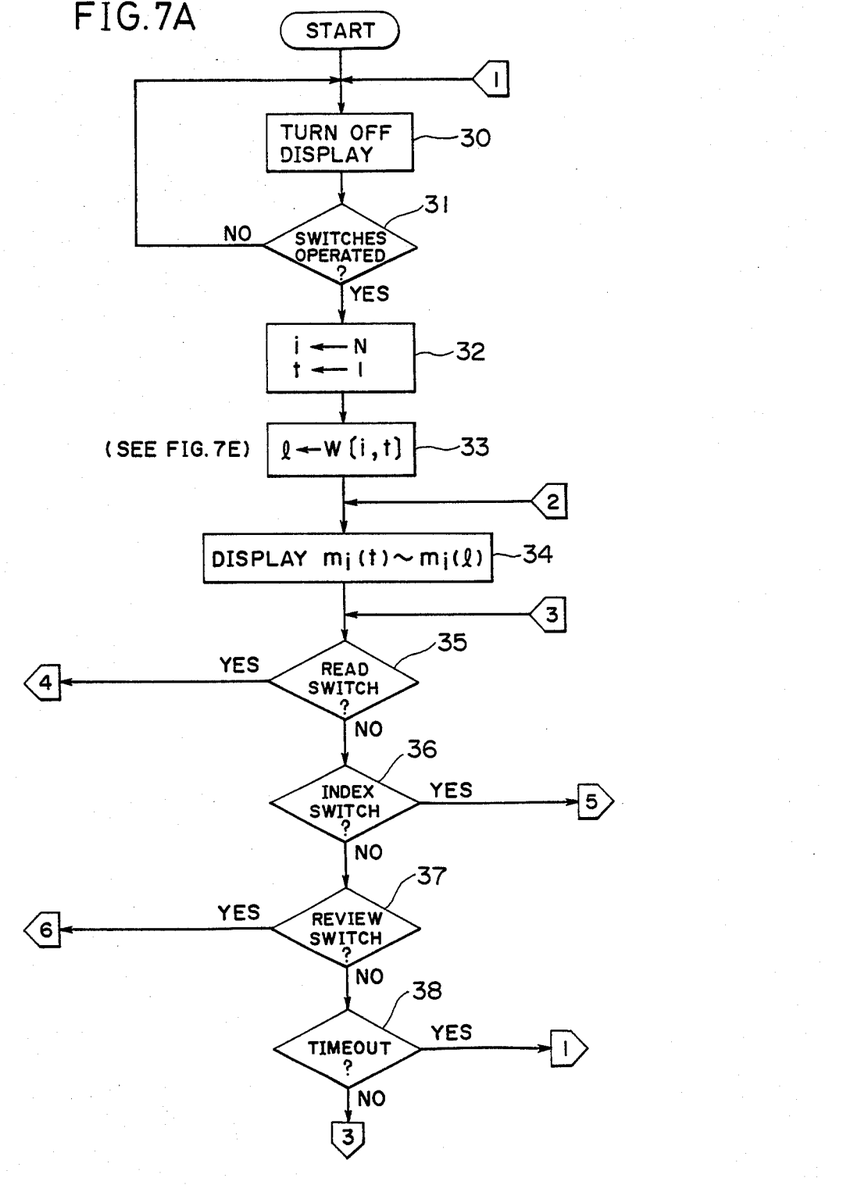
FIGS. 7A through 7F are flow diagrams describing a sequence of instructions performed by the microprocessor according to the second embodiment.

The messages stored in the form of FIG. 6 into the memory 10 are recalled by microprocessor 9 according to programmed instructions described in FIGS. 7A through 7F. In FIG. 7A, the program starts with display turn-off block 30 followed by decision block 31 to check for the operation of any of the command entry switches. Exit then is to operations block 32 which directs the setting of the variables i and t equal to N and 1, respectively, where N represent the most recent message as in the previous embodiment. Exit then is to operations block 33 which directs the setting of the variable t to a value which is determined as a function of variables i and l in a manner as will be described with reference to FIG. 7E. With the variables i, t and l being determined, control advances to operations block 34 which directs the displaying of characters and blanks identified $m_i(t)$ through $m_i(l)$. The Read, Index and Review switches 14, 13 and 15 are scanned as control performs decision blocks 35, 36, 37 and 38.

Figures 7B, 7C:
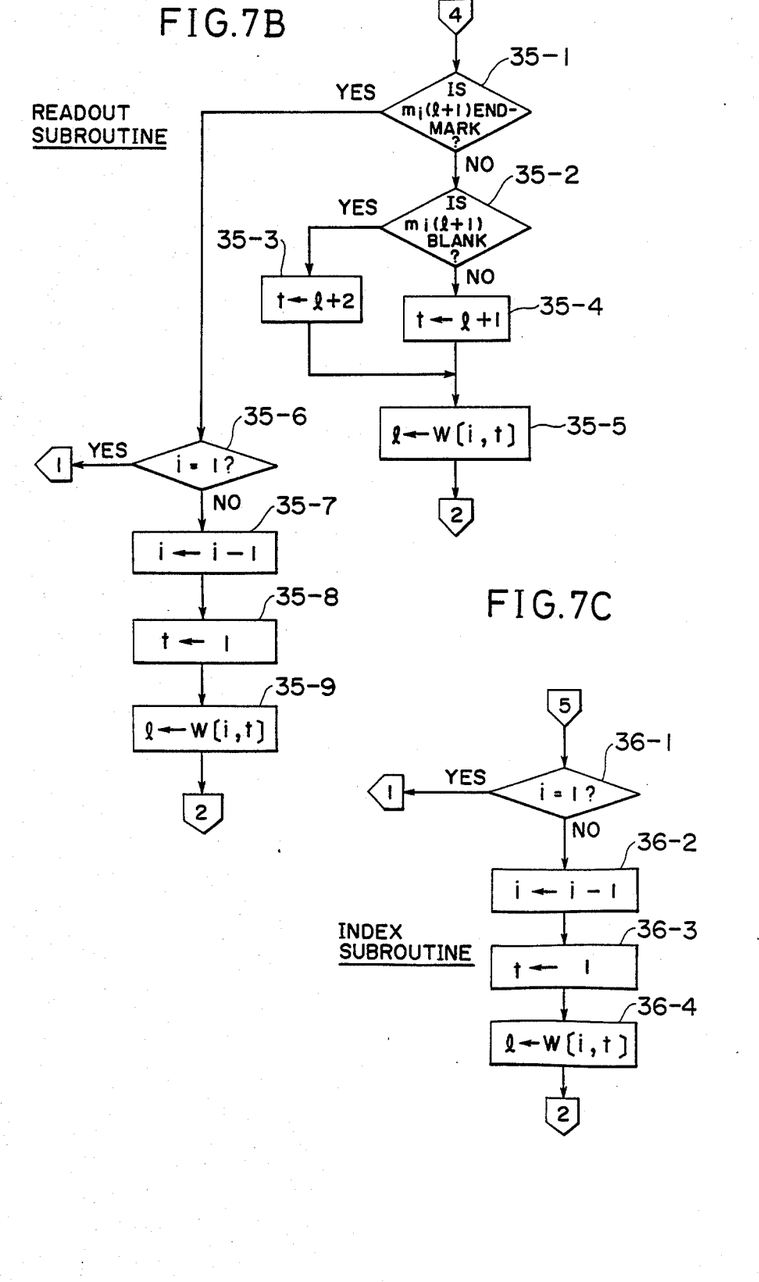
Figure 7D:
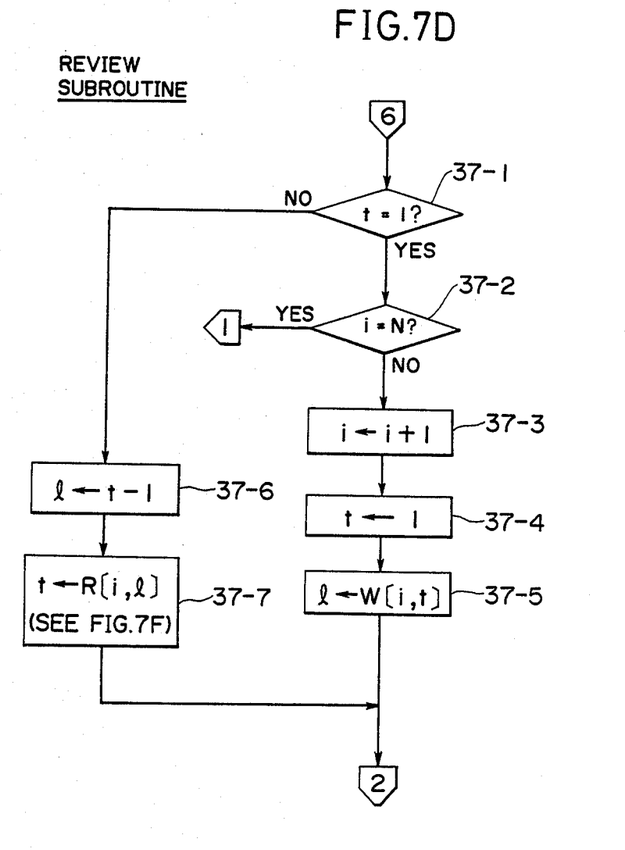
Figure 7E:
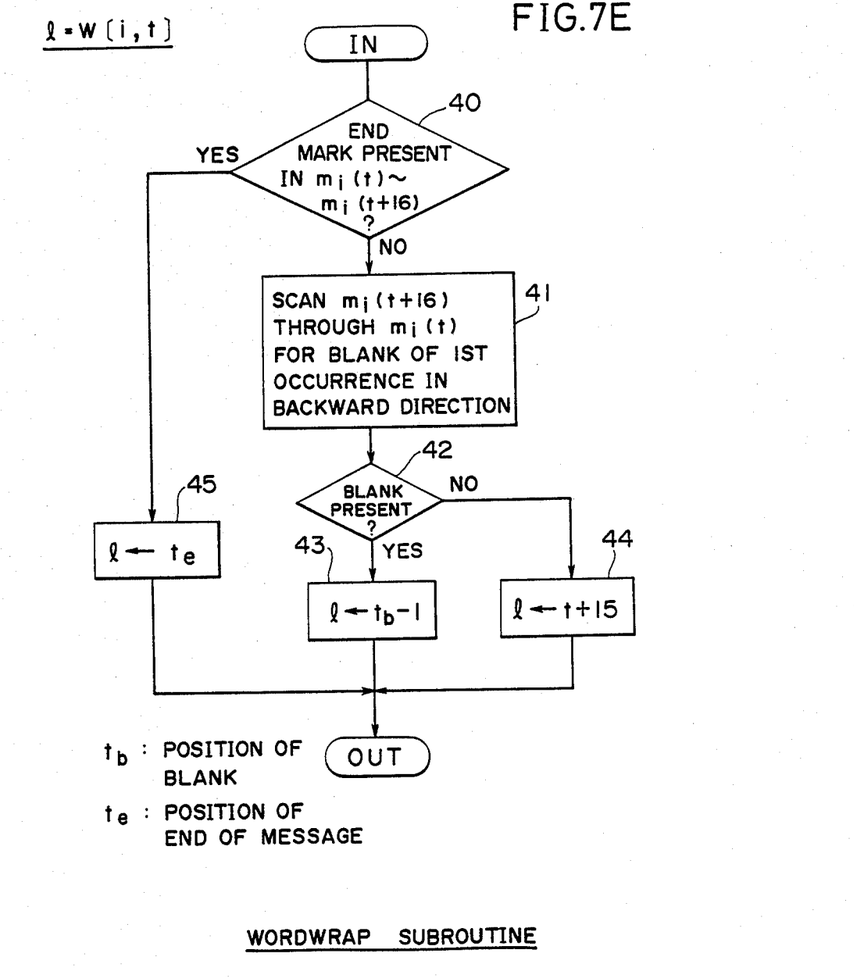

In FIG. 7E, a wordwrap subroutine is shown to determine the variable l as a function of variables i and t. The subroutine starts with decision block 40 which checks for the presence of an endmark in the position $m_i(t+16)$. If there is none, exit is to operations block 41 which directs the backward scanning of the characters $m_i(t+16)$ through $m_i(t)$ in search of a blank. Since the variable t is initially set equal to 1, the 17th through first characters of message $m_i$ are scanned backwards in search of a blank of first occurrence. If such a blank exists (block 42), operations block 43 is executed by determining the position of a character leftwardly adjacent the blank of first occurrence and representing it by a variable $t_b-1$ and setting the variable t equal to variable $t_b-1$. Thus, if the position $m_i(t+16)$ is filled with a blank, control recognizes that the last word of the whole character string is complete, and if $m_i(t+16)$ is not blank but $m_i(t+10)$, for example, is a blank of first occurrence, control recognizes that the last word is incomplete and the variable t is set equal to "$t+9$" to cause a wordwrap to occur in a position $m_i(l+9)$. If no blank is detected in any of positions $m_i(t+16)$ through $m_i(t)$, control recognizes that the whole character string extends beyond the maximum length. Therefore, if the answer is negative in block 42, exit is to operations block 44 which directs the setting of the variable t to $t+15$. If the answer is affirmative in block 40, exit is to operations block 45 which determines the position $t_e$ of the endmark and sets the variable t equal to $t_e$. Therefore, the incomplete last word is excluded from those which are to be displayed by operations block 34.

If the Read switch 14 is operated following the display of a first sequence of characters, control exits decision block 35 and executes a readout subroutine shown in FIG. 7B. The readout subroutine begins with decision block 35-1 which checks for the presence of an endmark in the position $m_i(l+1)$. If the answer is negative, exit is to decision block 35-2 which tests for the presence of a blank in the position $m_i(l+1)$. If there is one, exit is to operations block 35-3 which directs the setting of the variable t equal to 1+2 and if there is none, exit is to operations block 35-4 which directs the setting of the variable t equal to 1+1. In this way, the first position of the next message block to be displayed is filled with a character. Exit then is to operations block 35-5 which determines the variable t as a function of variables i and t in accordance with the wordwrap subroutine of FIG. 7E. Exit then is to operations block 34 to display wordwrapped data in positions $m_i(t)$ through $m_i(l)$. If the answer is affirmative in block 35-1, exit is to decision block 35-6 which tests for the presence of the variable i=1. If there is one, control returns to the display turn-off block 30, and if there is none, exit is to operations block 35-7 where the variable i is decremented by one to scroll one message in a backward direction in the memory 10. In decision blocks 35-8 and 35-9, variable t is set equal to 1 and variable l is determined as a "wordwrap" function of variables i and t in accordance with the wordwrap subroutine of FIG. 7E. Control now returns to message display block 34. Therefore, the message is scrolled to the first block of each message in a backward direction whenever an endmark is detected in block 35-1.

When the Index switch is operated, control exits block 36 to decision block 36-1 (FIG. 7C) which checks for the presence of the variable i=1. If there is one, exit is to the display turn-off block 30. If there is none, control exits to operations block 36-2 where the variable i is decremented by one to scroll one message in a backward direction. Exit then is to operations block 36-3 which directs the setting of the variable t to 1 to move the display window to the first block of a message "i". Variable l is subsequently determined as a function of variables i and t in accordance with the wordwrap subroutine of FIG. 7E. Control now exits to message display block 34. Therefore, the operation of the Index switch causes the display window to scroll from the first block of one message to the first block of another in a backward direction.

When the Review switch is operated, exit from decision block 37 is to decision block 37-1 (FIG. 7D) which tests for the presence of the variable t=1. If the display window is on the first block of a message "i", the answer is affirmative in block 37-1. Control advances to decision block 37-2 to check for the presence of the variable i=N. If the message being displayed is the most recent one, the answer is affirmative in block 37-2 and exit is to the display turn-off block 30. If not, the answer is negative in block 37-2 and exit is to operations block 37-3 where the variable i is incremented by one to scroll the display window one message in a forward direction.

Variable t is set equal to 1 in operations block 37-4 and variable l is determined as a function of variables i and t in accordance with the wordwrap subroutine (FIG. 7E). Therefore, if the display window is initially located in the first block of a message other than the most recent one, blocks 37-1 through 37-5 are repeatedly executed. The display window is scrolled from the first block of one message to the first block of another in a forward direction in response to each operation of the Review switch. On the other hand, if the display window is initially located on a block other than the first block of a message, the answer is negative in decision block 37-1 and exit is to operations block 37-6 where the variable t is decremented by one. The variable l is set equal to t−1 to determine the rightmost character.

In this manner, the rightmost character of the next message block coincides with the rightmost position of the display window. To determine the leftmost character of the next message block, control goes to operations block 37-7 to determine the variable t as a function of variables i and l in accordance with a "reverse word-wrap" subroutine shown in FIG. 7F. Control then returns to the message display block 34.

Figure 7F:
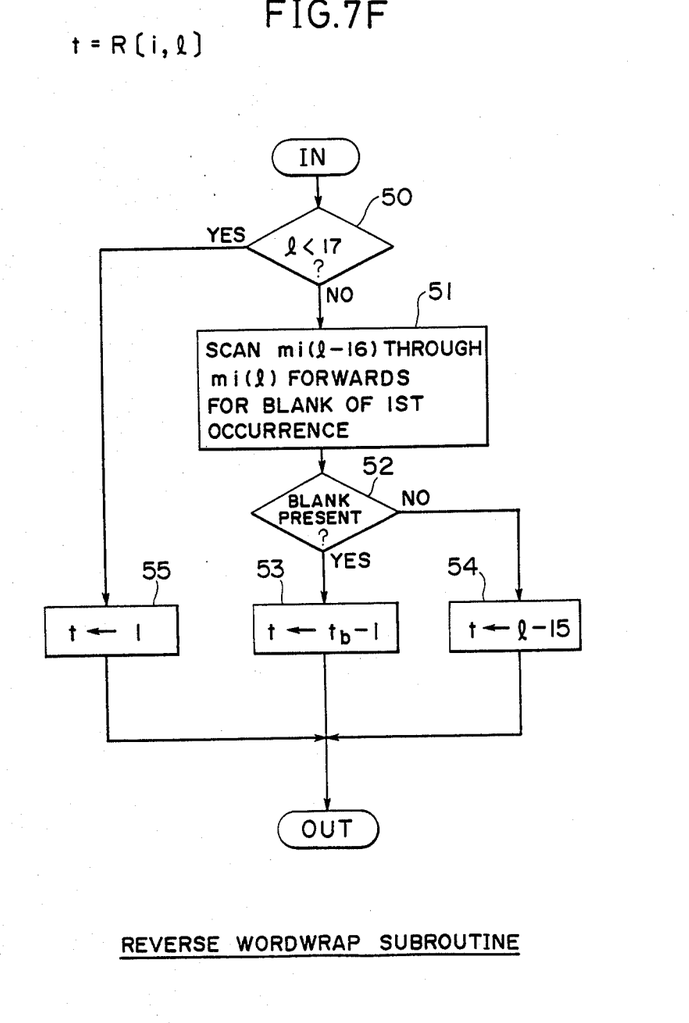

In FIG. 7F, the reverse wordwrap subroutine begins with decision block 50 which determines whether the variable l is smaller than "17". If the number of characters in a message to be initially displayed exceeds the maximum number of display elements, the answer will be negative in block 50 and exit is to operations block 51 which directs the scanning of characters $m_i(l+16)$ through $m_i(l)$ in a forward direction to detect a blank of first occurrence. If a blank is detected, control proceeds through blank detection block 52 to operations block 53 which determines the position $t_b$ of the detected blank and decrements $t_b$ by one and sets the variable t equal to $t_b - 1$. If a blank is not detected, exit is to operations block 54 which sets the variable t equal to l−15. If the answer is affirmative in block 50, exit is to operations block 55 which directs the setting of variable t to 1. It is seen, therefore, that the leftmost position of the display coincides with the beginning of a word.

The foregoing description shows only preferred embodiments of the present invention. Various modifications are apparent to those skilled in the art without departing from the scope of the present invention which is only limited by the appended claims. Therefore, the embodiments shown and described are only illustrative, not restrictive.

What is claimed is:

1. A selective calling radio pager having a display, comprising:
   detector means for receiving a signal containing a message destined to said pager;
   a memory for storing a plurality of said messages;
   manually operated first, second and third command entry means for respectively generating first, second and third command signals; and
   control means for (a) successively recalling portions of said messages from said memory in a first sequence in response to said first command signal and causing the recalled portions to be successively displayed in said display, (b) successively recalling starting portions of said messages from said memory in a second sequence in response to said second command signal and causing the recalled starting portions to be successively displayed in said display, and (c₁) successively recalling portions of one of said messages from said memory in a direction opposite to said first sequence in response to said third command signal if the portion being displayed at the moment said third command signal is generated is not a starting portion of a message and causing the recalled portions to be successively displayed in said display or (c₂) successively recalling the starting portions of said messages from said memory in a direction opposite to said second sequence in response to said third command signal if the portion being displayed at the moment said third command signal is generated is a starting portion of a message and causing the recalled starting portions to be successively displayed in said display.

2. A selective calling radio pager as claimed in claim 1, wherein each of said messages comprises a series of characters and blanks, said control means including means for scanning one of said stored messages in a direction opposite to said first sequence to detect a blank of first occurrence and excluding part of the scanned message which is located adjacent said detected blank from a portion of the message which is displayed when message portions are recalled in said first sequence or when starting portions are recalled in a direction opposite to said second sequence.

3. A selective calling radio pager as claimed in claim 2, wherein said control means further includes means for scanning one of said stored messages in said first sequence to detect a blank of first occurrence and excluding part of the scanned message which is located adjacent said detected blank from a portion of the message which is displayed when message portions other than the starting portions are recalled in a direction opposite to said first sequence.

4. A selective calling radio pager as claimed in claim 1, wherein each of said messages is divided into portions and the divided portions are stored in a matrix of rows and columns.

5. A selective calling radio pager as claimed in claim 2, wherein each of said messages is stored in the form of a continuous string, and the beginning of the string is identified by a pointer.

6. A selective calling radio pager as claimed in claim 3, wherein each of said messages is stored in the form of a continuous string, and the beginning of the string is identified by a pointer.

* * * * *